United States Patent
Matay

[11] 4,004,454
[45] Jan. 25, 1977

[54] ULTRASONIC INSPECTION METHOD OF PULSE REFLECTION DEFECT DETECTION USING A THRU-TRANSMISSION AUTOMATIC DISTANCE-AMPLITUDE COMPENSATION

[75] Inventor: Istvan M. Matay, North Royalton, Ohio

[73] Assignee: TRW Inc., Cleveland, Ohio

[22] Filed: May 7, 1975

[21] Appl. No.: 575,460

[52] U.S. Cl. ............................................. 73/67.8 R
[51] Int. Cl.² ...................................... G01N 29/04
[58] Field of Search .......... 73/67.7, 67.8 R, 67.8 S, 73/67.9, 67.5 R

[56] References Cited
UNITED STATES PATENTS

| | | | |
|---|---|---|---|
| 3,033,029 | 5/1962 | Weighart | 73/67.8 R |
| 3,690,153 | 9/1972 | Matay | 73/67.8 R |

Primary Examiner—Richard C. Queisser
Assistant Examiner—John P. Beauchamp

[57] ABSTRACT

An automatic distance amplitude correction device for automatically correcting for amplitude variations and signals caused by the attenuation of sound propagating through a test specimen wherein a signal is transmitted through a test specimen and the reflection is detected and furthermore, a through signal is detected after the signal has passed through the test specimen only a single time and utilized to provide improved automatic distance amplitude compensation.

10 Claims, 2 Drawing Figures

ULTRASONIC INSPECTION METHOD OF PULSE REFLECTION DEFECT DETECTION USING A THRU-TRANSMISSION AUTOMATIC DISTANCE-AMPLITUDE COMPENSATION

GOVERNMENT CONTRACT

The invention herein described was made in the course of or under a contract or subcontract thereunder with the United States Air Force.

BACKGROUND OF THE INVENTION

1. Field of the Invention

This invention relates in general to ultrasonic non-destructive test equipment for locating faults in test specimens.

2. Description of the Prior Art

Modern ultrasonic non-destructive test equipment provides for controlling the sensitivity of the receiver so as to adjust for the far-field characteristics of sound propagation through test specimens. Such units adjust for the ultrasonic beam energy-density characteristics as a function of the distance of sound travel from the transducer and also as a function of the distance for the attenuation characteristics caused by the material composition. Distance amplitude correction units (DAC) can be set for a particular transducer and a particular amount of attenuation. However, for material which have attenuation coefficients that greatly vary automatic distance amplitude correction is highly desireable. My U.S. Pat. No. 3,690,153 which issued on Sept. 12, 1972 is an example of an automatic distance amplitude correction unit which provides automatic correction for the variable response characteristics in ultrasonic tests which are caused by the materials internal structure. Variations in sound intensity result when the material in the path of travel of the ultrasonic beam reflects or absorbs more or less of the ultrasonic energy. The reflected energy in the ultrasonic wavefront that is returned to the transducer in pulse-echo tests is related to the dimensions of the defect encountered by the energy. If the energy arriving at a defect varies then the reflected energy from a defect will vary. Automatic distance amplitude correction apparatus such as described in U.S. Pat. No. 3,690,153 provides a more consistent display of defect images related to defect size by correcting for variable attenuation. The application of automatic distance amplitude correction according to the prior art is limited, however, by the signal strength (I) which is available after the interrogating pulse has travelled back and forth through the material (pulse-echo system). For example, where large attenuation exists due to either or both causes of excessive material cross-section (x) and high attenuation coefficient ($\alpha$), as for example, in a 16 inch diameter titanium alloy forging billet, the return echo from the opposite side of the material can be so weak that it has an amplitude less than the background noise and thus it is buried in the noise. Under these conditions, the return echo cannot be used for either manual distance amplitude correction apparatus or for automatic distance amplitude correction apparatus in conventional pulse reflection systems.

SUMMARY OF THE INVENTION

The present invention comprises an improved automatic distance amplitude correcting device and circuit for testing materials which utilizes a transducer for transmitting an ultrasonic beam through a test sample and receiving echoes from faults in the specimen and further includes a transducer for receiving energy which has passed through the test specimen only a single time and uses said single transit signal for automatic distance amplitude compensation. Thus, the apparatus of the present invention allows test samples having transverse dimensions much larger than those capable of being tested with prior art devices to be tested since in the pulse-reflection apparatus each pulse must pass through the exponentially attenuating material twice on is outgoing and incoming transits. The placement of a second transducer on the opposite side of the pulse reflection transducer makes it easy to sense acoustic energy which is passed through the test sample a single time in billets and test samples so large that the pulse reflection detection method is limited to a much smaller material thickness or the radius of the object if the test specimen is a cylindrical specimen.

In the present invention, the signal which is detected after a single passage through the specimen is used for automatic distance amplitude compensation.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure, and in which:

DESCRIPTION OF THE PREFERRED EMBODIMENTS

Figure 1:
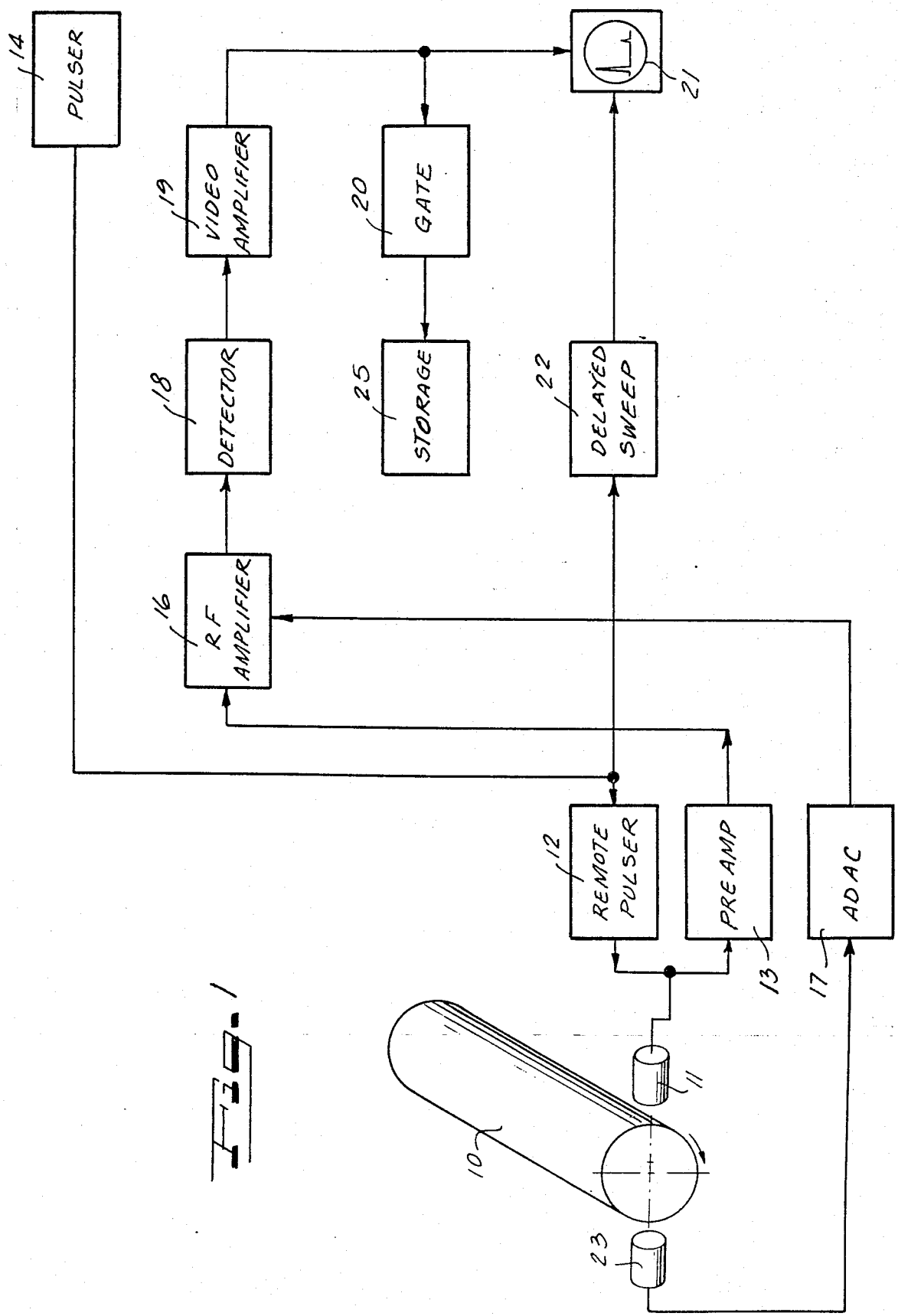
FIG. 1 is a block diagram of the testing system utilizing the automatic distance amplitude compensation of the present invention.

FIG. 1 is a block diagram according to the invention which illustrates a cylindrical test specimen 10 which might, for example, be a billet of 16 inch diameter titanium alloy. A pulser 14 periodically supplies an output to a remote pulser 12 which supplies an output to a transmitting and receiving transducer 11 which transmits ultrasonic pulses into the billet 10 and receives echoes therefrom for the pulse-reflection mode of inspection. A pre-amplifier 13 receives the outputs of the transducer 11 which comprise the received echoes and supplies an output to an RF amplifier 16 which has a variable gain. A detector 18 receives the output of the amplifier 16 and supplies an output to the video amplifier 19 which is connected to an A-scan display scope 21 as well as to a gate 20 for supplying a signal to a storage device 25. A delayed sweep generator 22 receives an output from the pulser 14 and supplies an input which has been delayed to the display device 21. An ultrasonic transducer for receiving through-type transmission and for supplying a signal to an automatic distance-amplitude correction unit is designated by 23 and supplies an output to an automatic distance-amplitude correcting unit 17 which supplies an output to control the gain of the RF amplifier 16.

Figure 2:
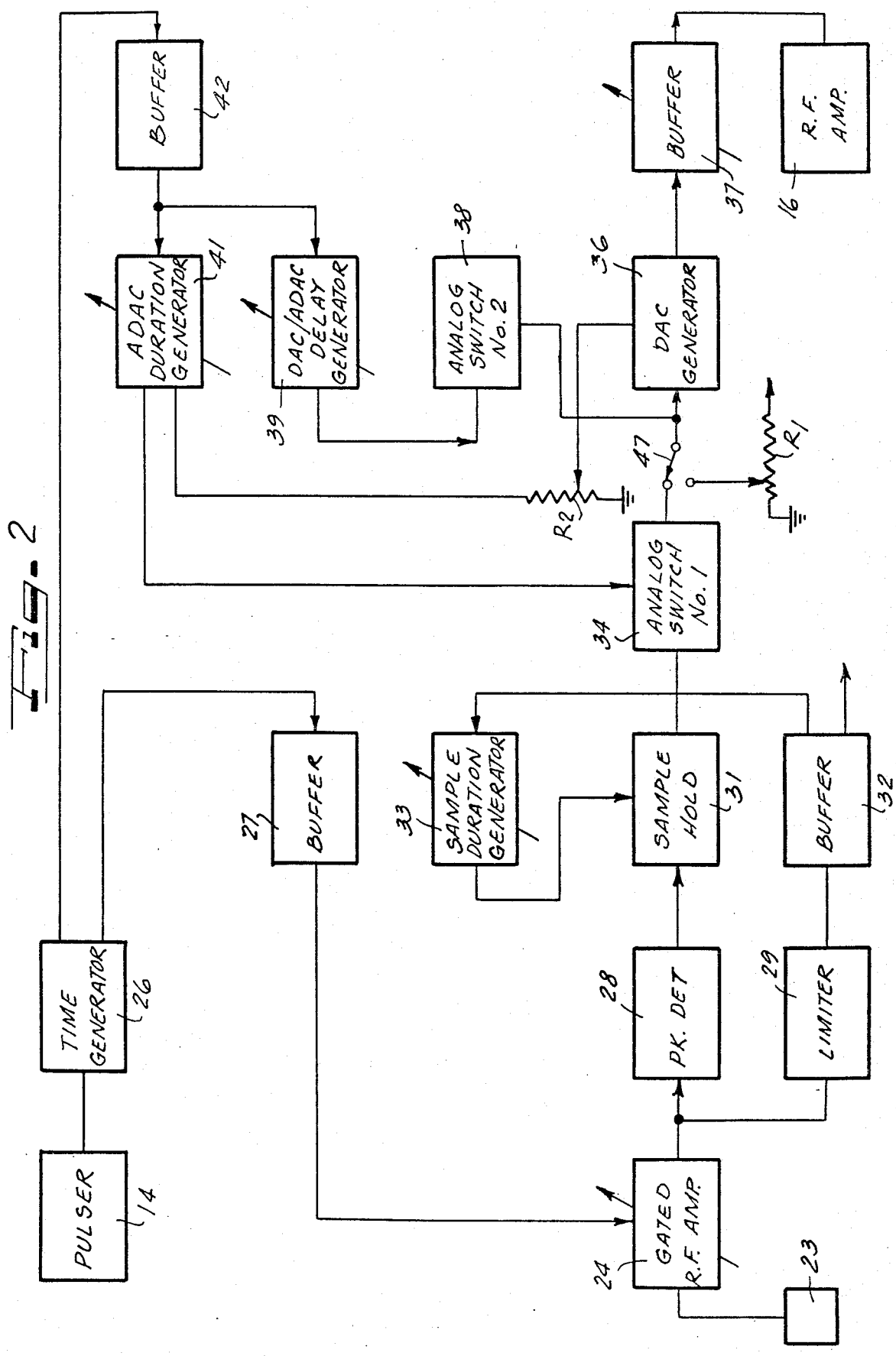
FIG. 2 is a block diagram of the automatic distance amplitude compensating unit.

FIG. 2 is a block diagram of the automatic distance amplitude correcting device 17. A time generator 26 supplies an output to the pulser 14 as well as a delayed time pulse to a buffer 27 which is connected to a gated RF amplifier 24 which receives an input from the transducer 23. The gated amplifier 24 passes the output of transducer 23 only during a short time interval which is when the interrogating acoustic pulse from transducer 11 is expected to arrive on the other side of the billet 10 at the transducer 23. By utilizing time gating the detection of spurious signals is substantially reduced. The transducer 23 detects the signal which has been transmitted through the billet 10 and passes it through the amplifier 24 to a peak detector 28 which supplies an output to the sample hold 31 which retains the peak output of the detector 28. The output of the sample hold circuit 31 is supplied through an analog switch 34 to an output terminal which is connected by a switch 47 to a distance amplitude correcting generator 36.

A limiter 29 also receives an output of amplifier 24 and supplies it to a buffer 32 which is connected to the sample duration generator 33 which is connected to the sample hold 31 to reset it if the "pass through pulses" exceed the previous average amplitude so that a new sample hold signal can be stored in the sample hold 31. The analog switch 34 is opened by the output of the automatic distance amplitude correcting duration generator 41 so as to supply the level of the signal stored in the sample hold 31 to the movable contact 47 and to the DAC generator 36. The output of the distance amplitude correction generator 36 is supplied to a buffer 37 which supplies an output to the gain control of the RF amplifier 16 to provide distance-amplitude correction. The switch 47 may be also connected to a wiper contact which engages a resistor R1 when automatic distance and amplitude correction is not required. A buffer 42 also receives an output pulse from the time generator 26 and supplies an output to a delay generator 39 and to a duration generator 41. The delay generator 39 supplies its output through an analog switch 38 to the generator 36. The duration generator 41 supplies an output to the switch 34 and to a resistor R2 which has a wiper contact that supplies an input to the generator 36.

The analogue switch 38, the generator 39 and ADAC duration generator 41 establish the gating time for the output through switch 34 to amplifier 16.

The present invention provides a consistent display of the defect images that might occur in the billet 10 as it is scanned by correcting for variable attenuation even in the case of extremely large acoustic attenuation. This is because the attenuation of the material is sensed in a unique manner by the through transmission transducer 23 and, thus, the effect of passage of the energy through the material (x) is reduced by ½ which in turn increases the signal strength several times due to the exponential nature of acoustic attenuation ($I=I_o e^{-\alpha x}$). As shown in FIG. 1, the billet 10 may be rotated such that the transducer 11 injects ultrasonic energy from the object's outside diameter to interrogate on a radial plane. Because of the large size of the billet and the resulting large attenuation, the pulse-reflection defect detection method would be limited to one-half of the thickness of the material or the radius of the object assuming it is a cylindrical object and back reflection from the cylinder's opposite side to that of the transducer 11 would not be sensed. However, by placing the through transducer 23 on the side of the billet opposite the transducer 11, the acoustic energy passing through the billet can easily be detected and the automatic distance amplitude compensation can be controlled by the transducer 23.

In operation, it is to be realized that the automatic distance amplitude compensation of the present invention is controlled by monitoring the pulse amplitude which passes through the test sample 10 and is detected by the transducer 23. The variation of the control signal supplied to the RF amplifier 16 depends on the amplitude of the signal received by the transducer 23 and as the signal received by the transducer 23 varies the exponential control signal output of the distance attenuation control generator 36 will vary as a function of the received signal in the manner described in my U.S. Pat. No. 3,690,153. However, it is to be realized that in my prior patent the control signal was generated by monitoring the pulse amplitude reflected from the rear innerface of the test specimen and reflected back to the transmitting transducer whereas in the present invention a separate transducer 23 detects the energy passing through the test specimen 10 and operates the automatic distance amplitude control module.

It is to be realized that the output of sample hold circuit 31 indicates the intensity of energy arriving at the through transducer 23 and this output level is supplied to generator 36 to adjust the gain of the RF amplifier 16. The control signal is supplied from transducer 23 and the actual circuitry for compensating for level variations may take the form of that shown in my U.S. Pat. No. 3,690,153.

Sample duration generator 33 resets the sample hold circuit 31.

Although this invention has been described with respect to preferred embodiments, it is not to be so limited as changes and modifications may be made which are within the full intended scope as defined by the appended claims.

I claim as my invention:

1. A pulse echo inspection device including a receiver having variable gain control means for testing a specimen comprising, first transducer means for periodically transmitting a signal into said specimen from one side thereof, and supplying echoes to said receiver, a second transducer means mounted on the opposite side of said specimen and receiving directly transmitted signals from said first transducer means, and an automatic distance-amplitude correcting device receiving the output of said second transducer means and producing a gain control signal which is supplied to said variable gain control means of said receiver.

2. A device according to claim 1 including means for indicating defects in said specimen connected to the output of said receiver.

3. A device according to claim 1 wherein said specimen is of a size and attenuation such that echoes from its center return to said first transducer means with sufficient intensity to be consistently detected and said second transducer means consistently detects energy from said first transducer.

4. A device according to claim 1 including a peak detector connected to said second transducer and a sample hold circuit connected to said peak detector, a distance amplitude correcting device, said sample hold circuit connected to said distance amplitude correcting device.

5. A device according to claim 4 including means for pulsing said first transducer means, a gated amplifier between said second transducer and said automatic distance amplitude correcting device and said gated amplifier passing signals during times when said second transducer means expects to receive energy from said first transducer means and said gated amplifier controlled by said means for pulsing said first transducer means.

6. A device according to claim 4 including a sample duration generator connected to said sample hold circuit to reset it, and means connecting said sample duration generator to said second transducer.

7. A device according to claim 6, including a time generator connected to said means for pulsing, a duration generator forming a part of said automatic distance amplitude correcting device and connected to said time generator.

8. A device according to claim 7 including, a delay generator forming a part of said automatic distance amplitude correcting device and connected to said time generator.

9. The method of testing specimens comprising,
transmitting ultrasonic energy into said specimen from one side and detecting echoes at said one side,
detecting ultrasonic energy on the other side of said specimen,
amplifying the echoes received on said one side and adjusting the amplifying gain as a function of the ultrasonic energy detected on said other side.

10. The method of claim 9 wherein detecting energy on said other side occurs during periods when energy from said one side is expected.

* * * * *